US006632964B2

(12) United States Patent
Fujii et al.

(10) Patent No.: US 6,632,964 B2
(45) Date of Patent: Oct. 14, 2003

(54) PROCESS FOR PRODUCTION OF ALIPHATIC ALDEHYDE-ACID AND/OR ALIPHATIC DICARBOXYLIC ACID AND CATALYST FOR THE PRODUCTION

(75) Inventors: Masaru Fujii, Kanagawa (JP); Tohru Setoyama, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/886,215

(22) Filed: Jun. 22, 2001

(65) Prior Publication Data

US 2002/0004609 A1 Jan. 10, 2002

Related U.S. Application Data

(63) Continuation of application No. PCT/JP99/07193, filed on Dec. 21, 1999.

(30) Foreign Application Priority Data

Dec. 22, 1998  (JP) ............................................ 10-365681
Dec. 22, 1998  (JP) ............................................ 10-365682

(51) Int. Cl.[7] ................... C07C 51/245; C07D 223/00; B01J 29/00; B01J 21/00
(52) U.S. Cl. ........................... 562/528; 502/60; 502/66; 502/74; 540/485; 540/534; 540/538; 562/577
(58) Field of Search ................................ 540/485, 534, 540/538; 502/74, 60, 66; 562/528, 577

(56) References Cited

U.S. PATENT DOCUMENTS

| 4,649,217 A | 3/1987 | Maki et al. .................. 562/528 |
| 5,776,423 A | 7/1998 | Feeley et al. ............. 423/239.2 |

FOREIGN PATENT DOCUMENTS

| EP | 0 091 091 | 10/1983 |
| EP | 0 519 569 | 12/1992 |
| JP | 41-21138 | 12/1941 |
| JP | 46-31538 | 9/1971 |
| JP | 47-26768 | 10/1972 |
| WO | 96/31455 | 10/1996 |

OTHER PUBLICATIONS

Yao et al., *Liquid–Phase Oxidation of Cyclohexanone To Dibasic Acids Over Supported Cerium Catalysts*, Chemical Engineering Science, vol. 47, No. 9–11, pp. 2745–2750, 1992.

F. Thibault–Starzyk et al., *Oxidation of Cyclohexanone and Cyclohexane to Adipic Acid by Iron–Phthalocyanine on Zeolite*, Studies in Surface Science and Catalysis, vol. 84, pp. 1419–1424, 1994.

Trost et al., *Ferric Salt Catalyzed Oxygenation of Cycloalkanones to Oxo Esters by Molecular Oxygen*, J. Org. Chem., 1983, 48, 1133–1135.

H.–C. Shen, et al., Ind. Eng. Chem. Res., vol. 27, No. 12, pp. 2246–2254, "Liquid–Phase Oxidation of Cyclohexanone to Dibasic Acids with Immobilized Cobalt Catalyst", 1998.

*Primary Examiner*—Porfirio Nazario-Gonzalez
(74) *Attorney, Agent, or Firm*—Oblon, Spivak, McClelland, Maier & Neustadt, P.C.

(57) ABSTRACT

A process of producing an aliphatic aldehyde-acid (e.g., adipaldehyde-acid) and/or an aliphatic dicarboxylic acid (e.g., adipic acid) comprising oxidizing a cyclic ketone (e.g., cyclohexanone) with molecular oxygen in the presence of a fixed catalyst which comprises a composite of a carrier and at least one metal element belonging to the groups 4 to 11 of the Periodic Table supported on the carrier and has an acid amount of 0.06 mmol/g or more per unit weight of the carrier.

31 Claims, No Drawings

PROCESS FOR PRODUCTION OF ALIPHATIC ALDEHYDE-ACID AND/OR ALIPHATIC DICARBOXYLIC ACID AND CATALYST FOR THE PRODUCTION

This application is a Continuation of International Application Ser. No. PCT/JP99/07193, filed Dec. 21, 1999.

TECHNICAL FIELD

This invention relates to a process for producing an aliphatic aldehyde-acid, particularly adipaldehyde-acid (5-formylpentanoic acid), and/or an aliphatic dicarboxylic acid, particularly adipic acid, by oxidation of a cyclic ketone and a catalyst useful for producing them. More particularly, the invention relates to a catalyst which comprises a carrier having fixed thereon a metal element belonging to the groups 4 to 11 of the Periodic Table, e.g., iron, and possesses specific properties (hereinafter referred to as a fixed catalyst or simply a catalyst) and a process of producing adipaldehyde-acid and/or adipic acid which comprises oxidizing a cyclic ketone, e.g., cyclohexanonone, in the presence of the catalyst. The invention also provides a process of leading adipaldehyde-acid to e-caprolactam.

BACKGROUND ART

Adipaldehyde-acid is a useful compound as an intermediate of syntheses. Known processes for production include, for example, oxidation of cyclohexanone with molecular oxygen in the presence of water and a copper compound (JP-B-47-26768, the term "JP-B" as used herein means an "examined Japanese patent publication) and oxidation of cyclohexanone with molecular oxygen in the presence of water and an iron or iridium compound soluble in the reaction system (JP-B-4-2583).

Because the catalyst used in these processes is an iron, iridium or copper compound that is soluble in a liquid phase, application of the processes to industrial scale production involves the following three problems. Firstly, where an iron-containing homogeneous catalyst is used in an oxidative reaction system of cyclohexanone with oxygen for a long time, iron atoms gather via an oxygen atom to form inert iron hydroxide, basic iron hydroxide, iron oxide, etc. so that the activity decreases with time. Secondly, a copper- or iridium-containing homogeneous catalyst has poor productivity due to a low reaction rate. Thirdly, where a compound made of the metal and a halogen as a counter ion, which generally exhibits high activity, is used as a catalyst, the existence of halogen in the system essentially requires that the equipment, such as a reactor, piping, etc., be made of a highly anti-corrosive material, which results in, of necessity, an increase of production cost.

DISCLOSURE OF THE INVENTION

The inventors of the present invention have conducted extensive investigation in order to solve the above-described problems. They have found as a result that a composite comprising a carrier having supported thereon a metal element belonging to the groups 4 to 11 of the Periodic Table, for example, iron and having specific acidity exhibits stable activity in the reaction for producing an aliphatic aldehyde-acid and/or an aliphatic dicarboxylic acid by oxidation of a cyclic ketone in a heterogeneous reaction system in the co-presence of molecular oxygen, particularly oxidation reaction of cyclohexanone to produce adipaldehyde-acid and/or adipic acid.

The present invention provides a novel process of producing an aliphatic aldehyde-acid and/or an aliphatic adipic acid by oxidation of a cyclic ketone, especially of producing adipaldehyde-acid and/or adipic acid by oxidation of cyclohexanone. The gist of the present invention consists in a process of producing an aliphatic aldehyde-acid and/or an aliphatic dicarboxylic acid characterized in that a cyclic ketone is oxidized with molecular oxygen in the presence of a fixed catalyst which comprises a composite of a carrier and at least one metal element belonging to the groups 4 to 11 of the Periodic Table supported on the carrier and has an acid amount of 0.06 mmol/g or more per unit weight of the carrier.

The present invention also relates to a catalyst for producing an aliphatic aldehyde-acid and/or an aliphatic dicarboxylic acid by oxidizing a cyclic ketone, especially adipaldehyde-acid and/or adipic acid by oxidizing cyclohexanone. The gist of this aspect of the invention lies in a fixed catalyst characterized by comprising a composite of a carrier and at least one metal element belonging to the groups 4 to 11 of the Periodic Table supported on the carrier and having an acid amount of 0.06 mmol/g or more per unit weight of the carrier.

The gist of the invention also resides in a process for producing e-caprolactam which comprises oxidizing cyclohexanone with molecular oxygen in the presence of a fixed catalyst comprising a composite of a carrier and at least one metal element belonging to the groups 4 to 11 of the Periodic Table supported on the carrier and having an acid amount of 0.06 mmol/g or more per unit weight of the carrier to produce an oxidation product containing adipaldehyde-acid, allowing the adipaldehyde-acid recovered from the oxidation product to react with ammonia and hydrogen in the presence of a hydrogenating catalyst to produce 6-aminocaproic acid, and heating the resulting 6-aminocaproic acid to cause cyclization into e-caprolactam.

Preferred embodiments of the present invention provide the above-described fixed catalyst wherein the metal element belonging to the groups 4 to 11 of the Periodic Table, which is supported on the carrier, is selected from iron, copper, and iridium, particularly an iron complex; and a process of producing an aliphatic aldehyde-acid and/or an aliphatic dicarboxylic acid, especially adipaldehyde-acid and/or adipic acid, which comprises oxidation in the presence of this catalyst and water.

BEST MODE FOR CARRYING OUT THE INVENTION

The present invention will be described in detail.

Carriers that can be used in the present invention include clay, ion-exchange resins, and metal oxides. Zeolite is preferably used. While zeolite to be used is not particularly limited in crystal structure, zeolites having channels greater than a 8-membered oxygen ring in at least one direction are preferred as channels constituting zeolile structures. Still preferred are those having channels of the above-specified condition in two or more directions, particularly three or more directions. Specifically, examples of preferred skeleton structure types are, according to the classification advised by IZA (International Zeolite Association), FAU, ERI, FER, BEA, MOR, MWW, MTW, MFI, and MEL.

In the fixed catalyst used in the reaction it is important for the carrier to have solid acidic properties. It is necessary for zeolite, for instance, to contain at least one M element selected from the group consisting of aluminum, gallium, indium, boron, etc. and at least one T element selected from the group consisting of silicon, germanium, tin, etc. in addition to oxygen as elements which constitute the zeolite skeleton. Aluminum is preferred as an M element, and silicon is preferred as a T element. A zeolite skeleton may comprise two or more kinds of the M elements and two or more kinds of the T elements. A zeolite skeleton may further comprise iron, titanium, zinc, manganese, chromium, cobalt, vanadium and zirconium. The molar ratio of these elements as represented by 2T/M (a value obtained by dividing the total mole number of T elements by a half of the total mole number of M elements) is preferably 9 or greater before supporting at least one metal element belonging to the groups 4 to 11 of the Periodic Table and is preferably 8 or greater after the supporting, and is preferably not greater than 300 either before or after the supporting.

It is preferred for zeolite as a carrier to have a specific surface area of 50 to 1500 $m^2/g$, particularly 100 to 1300 $m^2/g$, especially 150 to 1200 $m^2/g$.

Zeolite having too small a mean particle diameter has poor separability. One having too large a mean particle diameter has a reduced outer surface area, which makes the diffusion of the reaction substrate, the desired reaction product, etc. highly rate-determining. For these reasons, the mean particle diameter is desirably 0.01 $\mu$m to 10 $\mu$m, more desirably 0.02 $\mu$m to 8 $\mu$m, most desirably 0.03 $\mu$m to 6 $\mu$m. The term "mean particle diameter" refers to a number average of diameters of circles having the same areas as projected areas of crystals observed under a scanning electron microscope.

Where zeolite is used as a carrier, the fixed catalyst used in the present invention must contain at least one metal element belonging to the groups 4 to 11 of the Periodic Table in addition to the elements constituting the zeolite skeleton. The metal elements specifically include titanium, chromium, manganese, iron, cobalt, nickel, copper, and iridium. Preferred of them are iron, copper, and iridium. Iron is the most preferred. The fixed catalyst may contain two or more kinds of these elements.

In addition to the metal element belonging to the groups 4 to 11 of the Periodic Table, the fixed catalyst of the present invention can have part of zeolite displaced with cations of the group 1 elements, e.g., proton, lithium, sodium, potassium, and rubidium; the group 2 elements, e.g., magnesium, calcium and strontium; the group 12 elements, e.g., zinc; the group 13 elements, e.g., boron, aluminum and gallium; an ammonium ion, a tetraethylammonium ion, and the like. Too much displacement with metal elements such as sodium or ammonium ions reduces the acidity of the carrier. Therefore, in the case of FAU type zeolite, for instance, the Na/Al (by molar ratio) is usually 0.25 or less, preferably 0.15 or less.

Of the elements other than the metal elements of the groups 4 to 11 preferred are a proton and aluminum, with a proton being the most preferred.

The optimum amount of the metal element belonging to the groups 4 to 11 which is to be supported on the carrier varies depending on the element. Taking iron as an example, a suitable weight ratio of an iron element to the carrier is 0.001% to 60%, preferably 0.005% to 50%, still preferably 0.01 to 40%. Sufficient reaction activity is not obtained with lower amounts of the iron element supported than the above range. Too large an amount tends to be accompanied by, in addition to the catalytic activity, formation of inert by-products such as hydroxides and oxides in a low dispersed state.

There is no particular limitation imposed on the method of supporting the metal element belonging to the groups 4 to 11 on the carrier such as zeolite. An appropriate method is chosen from those commonly employed for catalyst preparation. Taking iron for instance, various methods can be adopted, including a liquid phase ion-exchange method using an iron compound soluble in a solvent, a solid phase ion-exchange method comprising mixing an iron compound powder and zeolite powder followed by heat treatment to introduce iron, a pore filling method comprising impregnating zeolite with a solution containing about as much iron as the pore volume of the zeolite followed by removing the solvent by evaporation to support iron, and a method comprising bringing zeolite into contact with vapor of a volatile iron compound followed by heat treatment to make an iron or iron oxide cluster grow in the pores of zeolite. The solvent used in the liquid phase ion-exchange method and the pore filling method is not particularly limited as long as it is capable of dissolving the iron compound. Various solvents such as water, methanol, ethanol and toluene can be used.

The fixed catalyst of the present invention which comprises a composite of the carrier and the metal element belonging to the groups 4 to 11 supported on the carrier has an acid amount of 0.06 mmol/g or more, preferably 0.08 mmol/g or more, still preferably 0.10 mmol/g or more, per unit weight of the carrier, when the acidity is measured by the acidimetry hereinafter described.

The compound containing the metal element belonging to the groups 4 to 11 which can be used for supporting on the carrier is not particularly limited. Useful compounds include inorganic acid salts of the metal, such as a nitrate, a sulfate, a phosphate, a chloride and a bromide; organic acid salts of the metal, such as an acetate, a tartrate and a citrate; organometallic compounds, such as carbonyl complexes (e.g., pentacarbonyliron) and ferrocenes; complexes having an organic ligand and/or an inorganic ligand, e.g., 1,2-ethylenediamine or acetylacetone; and complex salts. Preferred of them are a nitrate, a sulfate, a chloride, and a bromide.

The fixed catalyst of the present invention is preferably a composite prepared by supporting the metal element belonging to the groups 4 to 11 onto the carrier in a liquid phase. It is still preferred that a basic compound be present in the preparation system in a specific amount based on the metal element used in the supporting stage.

The basic compound which can be used in the preparation is preferably such that can dissolve in a requisite amount in the solvent used for supporting and is easily removed from the catalyst by a subsequent heat treating step. Compounds having such properties include the following compounds.

(1) Ammonia and hydrazine.

(2) Acyclic alkylamines or polyamines containing 1 to 4 nitrogen atoms and 1 to 12 carbon atoms, or acyclic alkylamines or polyamines having 1 to 4 nitrogen atoms and 1 to 4 substituents arbitrarily selected from the following substituent group (A) at arbitrary positions thereof including the nitrogen atoms and having a total carbon atom number of 1 to 12 exclusive of the carbon atoms in the substituents.

(3) Five- or six-membered cyclic alkylamines having 1 or 2 nitrogen atoms in the ring, or the alkylamines which have 1 to 3 substituents arbitrarily selected from the following substituent group (B) at arbitrary positions thereof including the nitrogen atoms.

(4) Five- or six-membered lactams having 1 or 2 nitrogen atoms in the ring, or the lactams which have 1 to 3 substituents arbitrarily selected from the following substituent group (B) at arbitrary positions thereof including the nitrogen atoms.

(5) Aromatic amines having one benzene ring.

(6) Five- to ten-membered heterocyclic aromatic compounds having 1 to 3 nitrogen atoms in the ring, or the heterocyclic aromatic compounds which have 1 to 3 substituents arbitrarily selected from the following substituent group (B) at arbitrary positions thereof including the nitrogen atoms.

(7) Quaternary ammonium salts having a hydroxide ion as a counter ion.

Substituent Group (A)

Hydroxyl group, methoxy group, ethoxy group, carboxyl group, formyl group, nitro group, cyano group, trifluoromethyl group, chlorine atom, fluorine atom, thiol group, methylthiol group, and sulfonic acid group Substituent Group (B)

Methyl group, ethyl group, 1-propyl group, 2-propyl group, hydroxyl group, methoxy group, ethoxy group, carboxyl group, formyl group, hydroxymethyl group, amino group, aminomethyl group, nitro group, cyano group, trifluoromethyl group, chlorine atom, fluorine atom, thiol group, methylthiol group, and sulfonic acid group.

Specific examples of the basic compounds are ammonia, hydrazine; methylamine, diethylamine, triethylamine, 1,2-ethylenediamine, 1,4-diazabicyclo[2,2,2]octane, triethanolamine; pyrrolidine, N-methylpiperizine; N-methylpyrolidinone, 2-piperidinone; aniline, hydroxyaniline; pyridine, pyrazine, pyramidine, pyrrole, imidazole, picoline, quinoline, 4-dimethylaminopyridine, 2,6-dimethylpyridine, 1,4-pyridinium hydroxide; and tetrabutylammonium hydroxide. Preferred of them are ammonia, methylamine, diethylamine, 1,2-ethylenediamine; pyridine, 4-dimethylaminopyridine, and 2,6-dimethylpyridine, with ammonia being particularly preferred.

The amount of the basic compound that can be present in the preparation of the composite is usually 0.01 to 50 times, preferably 0.05 to 20 times, still preferably 0.1 to 10 times, particularly preferably 0.2 to 5 times, the total mole number of the metal elements used in the supporting stage.

The term "supporting stage" as used herein denotes a series of steps including from the initial step of putting substances necessary for supporting into a container up to the step of conducting supporting.

The basic compound can be added in any step of the metal element supporting stage. In using zeolite, for example, the following methods (a) to (d) are commonly used.

(a) The basic compound is added to a solution containing the metal element, and zeolite is then added. (b) Zeolite and a solvent are brought into contact, and the basic compound is then added. Subsequently, a substance containing the metal element or a solution of a substance containing the metal element is added. (c) All substances necessary for supporting are added, and the basic compound is then added thereto. (d) All substances necessary for supporting are added, and after the mixture is heated up to a temperature necessary for supporting and treated at that temperature for a given time, the basic compound is added thereto. While an improving effect on the catalytic activity is produced whichever method is followed, method (c) or (d) is preferred because destruction of the zeolite structure is suppressed, and the metal element can be supported with good efficiency.

The temperature at which the basic compound is added is arbitrary within a range of from room temperature up to the supporting temperature. The addition is with or without agitation. The time required for all the amount of the basic compound to be added is usually 5 seconds to 2 hours, preferably 10 seconds to 1 hour, while varying according to the scale of supporting, etc. The basic compound to be added can be diluted with an appropriate solvent. Where the basic compound is gaseous at ambient temperature, the diluent may be a solvent or any other gas.

The operation for supporting the metal element in the presence of the basic compound can be conducted several times. It is possible that a carrier having supported thereon the metal element without using the basic compound is further treated for supporting in the presence of the basic compound. It is also possible that a supporting operation in the presence of the basic compound is followed by an ordinary supporting operation.

Where the supporting operation is performed several times, a heat treatment hereinafter described can be inserted between the supporting operations. Where a heat treatment is not conducted on the way, it is possible to omit a drying step between the supporting operations.

After the supporting operation, the resulting composite (sample) is usually separated by filtration or a like means, desirably washed with water, methanol, ethanol, etc., and then subjected to a drying step under atmospheric pressure or reduced pressure and a grinding step. The term "drying" as used herein refers to a step for making the washed sample lose the solvent into such a state as to exhibit properties as powder. While dependent on the kind of zeolite used, the "state" generally refers to a state with a solvent content equal to or less than the dry weight of the carrier.

The preparation of the fixed catalyst of the invention preferably includes a step of heat treating at 200 to 1100° C. The heat treating step can be carried out either before or after the introduction of the group 4 to 11 metal element into zeolite. The group 4 to 11 metal element can be introduced while heating the carrier in some cases but is preferably supported after the carrier has been heat treated. Where a base is added for supporting the metal element on the carrier as described above, it is important that the heat treatment be conducted after the metal supporting operation so that the base adsorbed on the carrier may be removed. As a matter of course, the metal element can be supported on a heat-treated carrier by use of the base, and the base is then removed by another heat treatment.

In case where the preparation of the fixed catalyst includes a step of introducing a group of organic compounds into the group 4 to 11 metal element/carrier composite as hereinafter described, it is essential that the heat treating step should be carried out before the organic compound is introduced into the carrier or the composite.

The heat treating step is performed at a temperature of 200 to 1100° C., preferably 300 to 1000° C., still preferably 400 to 900° C., particularly preferably 450 to 800° C. At temperatures lower than 200° C. the effect of improving the catalytic activity is inconsiderable. At too high temperatures exceeding 1100° C. the structure of the carrier itself, such as zeolite, may tend to be destroyed irreversibly.

The time for heat treating the carrier or the carrier/metal element (e.g., iron) composite is ordinarily 0.5 minute to 12 hours, preferably 1 minute to 6 hours. The "time for heat treating" is the time period in which the catalyst is substantially in the treating temperature. Influenced by the apparatus used, the amount of the catalyst, and the like, heat treatments that continue for seemingly the same treating time are not always equal in the practical treating time in the equipment.

Atmospheres which can be used in the heat treatment include inert gases such as nitrogen, argon, helium and carbon dioxide; mixed gases of an inert gas and oxygen, e.g., air; and oxygen. Nitrogen or air is preferred of them. These gases can contain up to 10% by volume of steam, nitrogen oxides, sulfur oxides or hydrogen chloride.

The gas used as an atmosphere is or is not made to flow during the heat treatment. The rate of flowing is usually 20/hr or less, preferably 10/hr or less, in terms of weight hourly space velocity (WHSV) based on the carrier or the carrier/metal element (e.g., iron) composite.

The heat treatment is generally effected under atmospheric pressure but may be conducted under pressure or under reduced pressure. It is carried out by means of an arbitrary heating apparatus such as a tubular furnace or a muffle furnace in a fixed bed system or a fluidized bed system.

The fixed catalyst of the present invention comprising the composite of the metal element belonging to the groups 4 to 11 and the carrier can further comprise an organic compound for the purpose of suppressing formation of by-products and dissolution of iron (element) into the liquid phase. Specific examples of the organic compounds that can preferably be used include compounds having a nitrogen-containing functional group, such as 1,2-ethylenediamine, 1,4-azabicyclo[2,2,2]octane, pyridine, 4-picoline, quinoline, 2,2'-bipyridyl, 1,10-phenanthroline, dimethylglyoxime, 1,2-cyclohexanedione.dioxime, aceto-hydroxamic acid, dimethylformamide, N-methylpyrrolidone, ethylenediaminetetraacetic acid, and porphyrin; compounds having an oxygen-containing functional group, such as 2,2'-biphenyldiol, 2,3-butanediol, acetylacetone, and 2-hydroxyacetophenone; and compounds having a nitrogen-containing functional group and an oxygen-containing functional group. Among them 2,2'-bipyridyl, 2,2'-biphenyldiol, 1,10-phenanthroline, and acetylacetone are suitable. They can be used in combination.

The stage and order of addition of the organic compound are not particularly limited. For example, the organic compound is added to the carrier before, after or simultaneously with the addition of the metal element belonging to the groups 4 to 11. In particular it is desirably added after the metal element belonging to the groups 4 to 11 is introduced. The amount of the organic compound to be added is preferably in a molar ratio of 0.001 to 20, particularly 0.01 to 10, to the amount of the group 4 to 11 metal element present in the carrier. The manner of adding the organic compound is not particularly limited. For example, a method comprising supporting the group 4 to 11 metal element on zeolite, adding the organic compound in a solid state, and introducing the organic compound onto the surface of, and/or into the inside of, the carrier by heating at room temperature or higher under reduced pressure or a method in which the carrier is brought into contact with the organic compound as dissolved in a liquid phase such as methanol can be employed. The method comprising a solid state contact is more convenient and preferred.

In the fixed catalyst of the present invention, the group 4 to 11 metal element supported on the carrier can take various states in the inside of, and/or on the outer surface of, the carrier. For example, iron can take the following state (1) or (2) or a mixed state thereof.

(1) In the Form of Iron Ion

Where iron can have a ligand, it can have coordinated thereto a molecule or an ion which may be led into the pores of the carrier together with iron in the step of supporting iron on the carrier or a molecule or an ion which may have been originally present in the pores, such as the aforementioned organic compound added, water, a hydroxide ion, a chloride ion, a bromide ion, and 1,2-ethylenediamine. One organic compound ligand can be coordinated to two or more iron atoms.

(2) In the Form of Metallic Iron Cluster or Iron Oxide Cluster

In this case, too, iron can have the same ligands as described in (1) above. The cluster as a whole is preferably zero- to trivalent in charge. While not limiting, one cluster is preferably made up of 2 to 11 iron atoms.

According to the process of the present invention, a cyclic ketone is cleaved by oxidation in the presence of the above-described fixed catalyst comprising a carrier having supported thereon at least one metal element belonging to the groups 4 to 11 to produce an aliphatic aldehyde-acid and/or an aliphatic dicarboxylic acid. The cyclic ketone used as a starting material is a saturated alicyclic monoketone having 4 to 7 carbon atoms, such as cyclopentanone, cyclohexanone, and cycloheptanone. Inter alia, cyclohexanone is especially useful.

The reaction conditions for carrying out the process of the present invention are shown below taking production of adipaldehyde-acid and/or adipic acid from cyclohexanone as an example.

In the production of adipaldehyde-acid and/or adipic acid according to the process of the present invention, the presence of water is not always essential but preferred for suppressing side reactions. A recommended amount of water to be used is about 0.01 to 1000 times, preferably about 0.05 to 100 times, still preferably 0.1 to 50 times, the weight of cyclohexanone. Depending on the amount of water, the liquid phase of the reaction system made up of cyclohexanone and water is a homogeneous phase or a suspended phase under the reaction temperature, either of which is effective. The term "water" as used herein indicates not only one supplied externally as a reaction substrate but one produced by the purposed reaction and side reactions. It is desirable that the total water content irrespective of origin be within the above-specified range.

The fixed catalyst is preferably used in a weight ratio of 0.005 or more to the cyclic ketone as a reaction substrate. The upper limit is decided within such a range that the slurry of the fixed catalyst and the liquid phase keeps fluidity at least under the reaction conditions.

In carrying out the process of the present invention, the reaction temperature is selected from a considerably broad range, which ranges, for example, from 0° C. to 200° C., preferably from 20° C. to 160° C., particularly from 40° C. to 140° C. The reaction proceeds sufficiently under atmospheric pressure, but pressure may be applied. The combination of temperature and pressure is desirably selected so that water and cyclohexanone may be kept in a liquid state.

The source of molecular oxygen which can be used in the reaction may be either pure oxygen or diluted oxygen such as air. The oxygen concentration is preferably higher than 10% so that the reaction may be conducted under a lower pressure. With the flammable limit of the gaseous phase being taken into consideration, a desirable oxygen concentration in the diluted gas is 1% to 10%. Diluent gases for oxygen include nitrogen, argon, carbon dioxide, neon, helium, hydrogen, butane, propane, ethane, and methane. Too low an oxygen partial pressure reduces efficiency of adipaldehyde-acid production. Too high an oxygen partial pressure can induce intractable side reactions such as autoxidation. Therefore, the oxygen partial pressure should be usually 0.01 to 2.0 MPa, preferably 0.02 to 1.0 MPa, particularly preferably 0.05 to 0.5 MPa, under the reaction conditions.

The reaction system can contain aliphatic hydrocarbons, aromatic hydrocarbons, oxygen-containing organic compounds, nitrogen-containing organic compounds, sulfur-containing organic compounds, halogen-containing organic compounds, and so forth. Examples of these compounds include hydrocarbons, such as benzene, cyclohexene, 1,3-cyclohexadiene, hexane, pentane, 1,1'-bicyclohexylidene, 3-cyclohexylidenecyclohexene, 1,1'-bicyclohexenyl, 1-cyclohexylcyclohexene, and dicyclohexyl; and alcohols, such as methanol, ethanol, 1-propanol, 2-propanol, 1-butanol, 2-butanol, 1,1-dimethylethanol, 1,2-ethanediol, cyclohexanol, cis- and trans-1,2-cyclohexanediol, cis- and trans-1,3-cyclohexanediol, cis- and trans-1,4-cyclohexanediol, 2-cyclohexen-1-ol, 1,6-hexanediol, 1,5-hexanediol, 2,5-hexanediol, 2-(1-cyclohexenyl)-cyclohexanol, 2-cyclohexylidenecyclohexanol, 2-cyclohexylcyclohexanol, and 1-(1-cyclohexenyl)-cyclohexanol.

Also included are oxygen-containing organic compounds, such as acetone, 2-hydroxycyclohexanone, 3-hydroxycyclohexanone, 1,2-cyclohexanedione, 2-cyclohexen-1-one, 3-cyclohexen-1-one, 1,2-epoxycyclohexane, 3,4-epoxycyclohexene, 2,3-epoxycyclohexan-1-one, caprolactone, 6-hydroxyhexanal, 5-hydroxyhexanal, 5-hexenal, 1,6-hexanedial, 2-(1-hydroxycyclohexyl)-cyclohexanone, 2-(2-hydroxycyclohexyl)-cyclohexanone, 2-(1-cyclohexenyl)-cyclohexanone, 2-cyclohexylidenecyclohexanone, 2-cyclohexylcyclohexanone, and dicyclohexyl ether; organic peroxides, such as hydroperoxycyclohexane, 3-hydroperoxycyclohexene, 4-hydroperoxycyclohexene, 2-hydroperoxycyclohexanone, 3-hydroperoxyyclohexanone, 4-hydroperoxycyclohexanone, 2-hydroperoxycyclohexanol, 3-hydroperoxycyclohexanol, and 4-hydroperoxycyclohexanol; carboxylic acids or carboxylic acid derivatives, such as monomethyl adipate, dimethyl adipate, pentanedicarboxylic acid, monomethyl pentanedicarboxylate, dimethyl pentanedicarboxylate, butanedicarboxylic acid, monomethyl butanedicarboxylate, dimethyl butanedicarboxylate, 6-hydroxyhexanoic acid, methyl 6-hydroxyhexanoate, 5-formyl-6-hydroxyundecanedicarboxylic acid, 5-formyl-5-undecenedicarboxylic acid, 6-(2-oxocyclohexyl)-6-hydroxyhexanoic acid, 6-(2-oxocyclohexylidene)-hexanoic acid, 5-(1-hydroxycyclohexyl)-5-formylpentanoic acid, 5-cyclohexylidene-5-formylpentanoic acid, and 5-(1-cyclohexenyl)-5-formylpentanoic acid; halogen-containing organic compounds, such as 2-chlorocyclohexanone; and compounds derived from the organic compounds added to the catalyst, such as 2,2'-bipyridyl, 2,2'-biphenyldiols, 1,10-phenanthroline, acetylacetone, and dibenzo[b,d]furan.

Of these compounds an arbitrary compound equivalent to an aldehyde or a ketone may be present in the form of an acetal and/or a ketal or a hemiacetal and/or hemiketal with an arbitrary alcohol compound, such as methanol, ethanol, 1-propanol, 2-propanol, 1-butanol, 2-butanol, 1,1-dimethylethanol, cyclohexanol, 2-cyclohexenol or 2-hydroxycyclohexanone. Further, an arbitrary compound equivalent to an aldehyde or a ketone may be present in the form of a condensation product which is derived by aldol condensation, or aldol condensation followed by dehydrating reaction, with an arbitrary compound equivalent to an aldehyde or a ketone. The two compounds equivalent to an aldehyde or a ketone may be the same or different. There may also be a compound derived by aldol condensation, or aldol condensation followed by dehydrating reaction, between two carbonyl groups present per molecule. There may also be a compound formed by esterification between an arbitrary carboxylic acid as enumerated above and an arbitrary alcohol as enumerated above. There may be a compound formed by ether bonding of an arbitrary alcohol in the reaction system.

When the above-described compounds except methanol, ethanol, 1-propanol, 2-propanol, 1-butanol, 2-butanol, 1,1-dimethylethanol and 1,2-ethanediol exist in the reaction system in large quantities, side reactions are apt to take place to give adverse influences on the catalyst activity. Therefore, it is usually preferred that the content of each of them in the reaction mixture be not more than 20 wt %, desirably not more than 10 wt %, more desirably not more than 5 wt %, based on the total weight of the liquid phase. The above-mentioned alcohols, on the other hand, are permitted to exist in a total proportion of up to 90 wt % based on the total liquid phase weight.

The reaction system may further contain, in its aqueous phase and/or organic phase, ions, complexes, clusters, ionic clusters, oxides, ionic metal oxide clusters, hydroxides, metal oxide colloids, etc. which are derived from the groups 4 to 11 metal elements in a concentration up to 15% by weight, preferably up to 10% by weight. The ligands coordinating to the metal element and the valency of the metal element are not particularly limited.

Additionally the aqueous phase and/or organic phase of the reaction system may contain cations of the group 1 elements, e.g., sodium ions and potassium ions, cations of the group 2 elements, e.g., magnesium ions and calcium ions, cations of the group 13 elements, e.g., aluminum ions, and the like in a concentration of up to 15% by weight, preferably up to 10% by weight, based on the fixed catalyst.

The reaction time or residence time of the oxidation reaction according to the present invention usually preferably ranges from 10 seconds to 10 hours, more preferably 1 minute to 7 hours, while varying depending on the reaction conditions, the reaction system, and the like. The reaction system may be either batch-wise or continuous. The type of the reactor is arbitrarily chosen from a stirred suspended bed system, a fixed bed system, a fluidized bed system, and the like. For industrial advantage the reaction is usually carried out in a continuous manner by use of a stirred suspended bed system. In what follows the oxidation reaction of cyclohexanone will be described with specific reference to the continuous stirred suspended bed system.

[Outline of Reaction Mode]

While the reaction mode is arbitrary, the following mode can be used for example. Water, cyclohexanone, and an oxygen-containing gas supplying molecular oxygen are continuously fed to a reactor in which the fixed catalyst of the present invention has been put. In parallel, the reaction mixture comprising formed adipaldehyde-acid and adipic acid and unreacted cyclohexanone is withdrawn continuously. The withdrawn reaction mixture is sent to a gas separation tower, where gas is separated and returned to the reactor. The reaction mixture is separated into an organic layer and an aqueous layer containing the fixed catalyst, which aqueous layer is returned to the reactor. The organic layer containing the desired products is forwarded to a distillation tower, where it is separated into unreacted cyclohexanone and other compounds including the desired products, i.e., adipaldehyde-acid and adipic acid, and by-products. The recovered cyclohexanone is returned to the reactor, and unnecessary by-products are purged. Where the by-produced phase contains valuable compounds, they could be recovered in the distillation step. When separation of the water-containing reaction mixture discharged from the reactor into the organic layer and the aqueous layer is insufficient, and the organic layer separated contains the insoluble fixed catalyst, the fixed catalyst is separated therefrom, the resulting organic layer is extracted with an organic solvent, and the organic solvent layer is led to the distillation tower, where the desired products, etc. can be separated.

[Method of Feeding Raw Materials]

1. At the Start of Reaction

After the start of reaction there are at least the fixed catalyst, cyclohexanone, and oxygen-containing gas in the reactor. The order to adding these materials into the reactor in initial charging is not particularly restricted, but it is preferable for reducing formation of by-products that water be co-present in the reaction system and that a contact between cyclohexanone and the fixed catalyst in the absence of water be avoided. Where water is used in the reaction, the following manners of mixing and charging are preferably used as specific order of addition.

(1-1): After the fixed catalyst is put into the reactor, water is added, and cyclohexanone is then added thereto.

(1-2): Cyclohexanone is the first to be added to the reactor. Water is then added, followed by addition of the fixed catalyst.

(1-3): Cyclohexanone is added to the reactor. A water dispersion previously prepared by slurrying the fixed catalyst in water is then added.

(1-4): A water dispersion previously prepared by slurrying the fixed catalyst in water is added to the reactor, and cyclohexanone is then added.

(1-5): The fixed catalyst, water, and cyclohexanone are mixed in a separate container for initial charging according to any of the methods (1-1) to (1-4) to prepare a suspension, which is forwarded to the reactor in the form of suspended slurry.

The fixed catalyst used here may previously contain an adequate amount of water as long as the properties as powder are retained. For example, a catalyst comprising FAU type zeolite as a carrier may have a water content equal to or less than the dry weight of the zeolite/metal element composite. Where the reaction temperature exceeds room temperature, the heating can be started in any stage of the methods (1-1) to (1-5).

It is preferred that each of the fixed catalyst, water and cyclohexanone to be put into the reactor be previously brought into contract with oxygen-containing gas. The oxygen concentration of the oxygen-containing gas used here does not always need to be the same as that of the reaction condition. Agitation of the reaction mixture and circulation of the oxygen-containing gas can be commenced in any of the stage for feeding each of the fixed catalyst, water, and cyclohexanone, or, where the reaction temperature is higher than room temperature, in the stage for elevating the temperature of the reactor or after completion of the temperature elevation. Agitation and circulation of the oxygen-containing gas do not always need to be commenced at the same time.

2. During Reaction

Feed of Raw Material (oxygen)

Cyclohexanone and oxygen in the reactor decrease with the progress of oxidation. It is therefore preferred to continue the reaction while replenishing the reactor with cyclohexanone and oxygen.

Oxygen can be supplied according to any one of the following embodiments.

(2-1): A cooling unit is fitted to the upper part of the reactor for refluxing cyclohexanone, water, etc., and an oxygen-containing gas is made to flow in the cooling unit at a certain fixed flow rate or under a certain fixed pressure thereby to supply oxygen continuously.

(2-2): A cooling unit is fitted to the upper part of the reactor for refluxing cyclohexanone, water, etc. An oxygen-containing gas is made to flow in the cooling unit to supply oxygen continuously while varying the flow rate or oxygen partial pressure of the oxygen-containing gas according to the readings of the oxygen concentration in the reactor.

(2-3): The same as in (2-1) or (2-2), except that the oxygen feed opening is submerged in the reaction liquid.

(2-4): The pressure of the reactor is maintained constant. A pressure loss accompanying the progress of the reaction is compensated for by addition of pure oxygen or a mixture of pure oxygen and diluent gas is fed according to the readings of the oxygen concentration in the reactor, thereby to keep the total pressure and the oxygen partial pressure in the reactor constant.

Where an oxygen-containing gas is made to flow, the oxygen feed rate is preferably such that the ratio of the oxygen feed rate (mol/hr) to the cyclohexanone feed rate (mol/hr) is from 0.01 to 200, particularly 0.05 to 100. Where an oxygen-containing gas is fed directly into the reaction mixture, the shape and size of the feed opening are not particularly limited. The feed opening may be on the shaft of an agitator or an agitating element or may be independently provided.

Feed of Raw Material (Cyclohexanone)

Cyclohexanone is fed to the reactor by either of the following embodiments. The method (3-1) is preferred for reaction stabilization.

(3-1): Cyclohexanone is continuously fed to the reactor.

(3-2): Cyclohexanone is intermittently fed to the reactor at certain time intervals.

[Reactor]

The reactor is not particularly limited. General reactors, such as a stirred tank reactor, a reactor made of two or more stirred tanks connected to each other, and a tubular reactor, can be used.

Materials of the reactor is not particularly limited, either. Various materials can be used unless corrosion proceeds considerably under the reaction conditions. Examples of useful materials are stainless steel, Hastelloy, Monel metal, inconel, titanium, titanium alloys, zirconium, zirconium alloys, nickel, nickel alloys, tantalum, fluoropolymer-lined materials, rubber-lined materials, glass-lined materials, and various kinds of glass.

[Method of Reaction]

The reaction is carried out with or without agitation. The reaction with agitation is preferred. The agitation power is preferably 0.05 to 50 W/l, still preferably 0.1 to 10 W/l, per volume of the reaction mixture inclusive of the fixed catalyst. Too much agitator power tends to crush the fixed catalyst, resulting in reductions of separability of the fixed catalyst and the catalyst activity. The agitator can have one or more than one shafts per tank. The shaft of the agitator is set in the upper or lower part or the side of a tank or in the intermediate angle between them. The mode of agitation includes, but is not limited to, center agitation, center agitation with the shaft inserted from the bottom of a tank, eccentric agitation, and lateral agitation.

The number of blades of an agitating element is not particularly limited and is appropriately selected from 1 to, e.g., 10. Any type of agitating elements can be used. Examples of useful agitating elements include a propeller, an inclined flat blade, a pitched flat blade, a flat blade disk turbine, a flat blade (turbine), a paddle, a curved blade, a Pfaudler type, a Brumagin type, a helical blade, an anchor blade, a perforated paddle, a scabbard impeller, and a Bernd disk turbine. In order to increase efficiency of mixing liquid phases and to increase contact efficiency with a gaseous phase, the reactor can be equipped with a turning blade, a baffle plate, a draft tube, etc. If necessary, a metal (iron) compound can be fed continuously to the reactor in a form soluble in water or cyclohexanone.

[Method of Separating Reaction Mixture]

The method for separating the reaction mixture is not particularly restricted. For example, the following embodiments are adopted. Methods (4-1) and (4-2) are preferred of them from the standpoint of reducing burdens such as filter clogging.

(4-1): A catalyst separation tank is provided inside or outside the reactor, and only the liquid phase (organic layer) is taken out while avoiding incorporation of the fixed catalyst.

(4-2): A catalyst separation tank is provided inside or outside the reactor, and only the liquid phase (organic layer) is taken out while avoiding incorporation of the fixed catalyst. The liquid phase (organic layer) is further passed through a filter to remove a trace amount of the incorporated fixed catalyst.

(4-3): A filter is provided inside or outside the reactor, through which the fixed catalyst is separated to recover the liquid phase.

The catalyst separation tank as used herein is a unit for separating the liquid phase from the fixed catalyst by making use of density difference, such as a stationary tank or a centrifuge.

Two or more catalyst separation tanks or two or more filters can be used as connected in parallel or in series or in a combination of parallel connection and series connection. For the purpose of improving organic layer/aqueous layer separability, the reaction mixture may be cooled or allowed to cool to lower temperatures than the reaction temperature in the catalyst separation tank.

[Method of Returning]

When the reaction mixture discharged from the reactor is allowed to stand and, if desired, passed through a filter to obtain a liquid phase (aqueous layer, etc.) containing the fixed catalyst and the liquid phase is returned to the reactor, or when cyclohexanone recovered by distillation (hereinafter described) is returned to the reactor, it is preferred that the liquid phase containing the fixed catalyst or the recovered cyclohexanone be returned to the reactor at a temperature exceeding (the reaction temperature −60° C.), particularly (the reaction temperature −50° C.). Compressed gas can be used for returning. While not particularly limiting, the same gas as used in the reaction, the same gas as used in the reaction and diluted with other inert gas, or an inert gas is preferably used. The inert gas includes nitrogen, argon, carbon dioxide, neon, and helium.

When oxygen-containing gas is returned to the reactor, the temperature is arbitrary but is preferably between room temperature and the reaction temperature. Where the returned gas has a higher temperature than room temperature, it can be utilized as a heating medium for the reactor.

[Method of Extraction]

Where the reaction mixture is allowed to stand to separate into an organic layer and an aqueous layer, and the organic layer is filtered to separate the accompanying fixed catalyst, the resulting liquid phase (organic layer) can be extracted with an organic solvent. Extracting solvents include aromatic hydrocarbons, esters, ethers, and ketones. Of these compounds, benzene, toluene, xylene, ethyl acetate, methyl isobutyl ketone, and cyclohexanone are preferably used, with cyclohexanone being the most preferred. The extracting temperature, while arbitrary, is preferably between room temperature and the reaction temperature.

[Method of Distillation]

Distillation is a preferred step for finally recovering adipaldehyde-acid or adipic acid as a product. The following method is followed, for example. The mixture mainly comprising organic compounds which is separated from the reaction mixture and/or the extract thereof is distilled in a first column to separate unreacted cyclohexanone or cyclohexanone used as an extracting solvent and low-boiling compounds from the reaction mixture. The mixture obtained from the bottom is further distilled in a second column to take out a final product, adipaldehyde-acid, from the top. Adipic acid of high added value is taken out from the mixture collected from the column bottom.

[Method of Stabilizing Catalyst Activity and Method of Catalyst Activation]

In case the catalyst activity is deteriorated with time to make the reaction instable, it is desirable that (1) part of the reaction mixture be taken out continuously, subjected to activation treatment for the fixed catalyst in the mixture, and returned to the reaction system or (2) a fresh fixed catalyst, a metal element-containing compound as supported on a carrier, a necessary organic compound, or a like substance is continuously supplied to the reactor to maintain the catalyst activity in the reactor on a given level. The manipulations (1) and (2) can be used in combination.

Any of the following methods can be used for activation of the fixed catalyst. If necessary, these methods can be used as a combination thereof.

(5-1): Treatment with an aqueous acid solution.

(5-2): Treatment with an aqueous alkali solution.

(5-3): Treatment with an oxidizing agent.

(5-4): Treatment with a reducing agent.

(5-5): Removal of substances adhering to the fixed catalyst with a solvent.

(5-6): Treatment with a supercritical fluid.

(5-7): Heat treatment at a temperature of 100° C. or higher.

(5-8): Liquid phase or vapor phase replenishment with a metal element, an organic compound, etc. to compensate the loss due to dissolution from the fixed catalyst.

(5-9): Removal of low-boiling compounds by reducing the pressure to 50 kPa or lower.

The fixed catalyst having been treated for activation can be returned to the reactor in a dried state, a slurried state in water, cyclohexanone, etc., or in a cake state containing water, cyclohexanone or another solvent. The term "dried state" means the state of the fixed catalyst retaining the properties as powder. Provided that this conditions is met, the fixed catalyst can have an appropriate water content. The temperature of the fixed catalyst while being returned to the reactor is suitably between room temperature and (reaction temperature +30° C.), preferably between room temperature and (reaction temperature +20° C.).

Adipaldehyde-acid obtained by oxidation of cyclohexanone according to the above-described process is useful as an intermediate material for various synthetic products. Inter alia, adipaldehyde-acid can be allowed to react with ammonia and hydrogen in the presence of a hydrogenation catalyst to produce 6-aminocaproic acid, which is led by heating to e-caprolactam that is a starting material of nylon-6.

6-Aminocaproic acid is produced by allowing adipaldehyde-acid and/or an adipaldehyde-acid derivative to react with excessive ammonia and hydrogen in the presence of a hydrogenation catalyst usually at a temperature of 30 to 300° C. under pressure, or amidating adipaldehyde-acid and/or an adipaldehyde-acid derivative with ammonia and then allowing the product to react with hydrogen. The adipaldehyde-acid derivative is a substance which is chiefly derived in the above-described preparation of adipaldehyde-acid. A mixture comprising two or more kinds of different derivatives may be used. Specific examples of the derivatives are adipaldehyde-acid esters, adipaldehyde-acid acetal, and adipaldehyde-acid ester acetals. Alcohols which are precursors of the esters or acetals are usually those having 1 to 4 carbon atoms, preferably methanol, ethanol, n-propanol, isopropyl alcohol, n-butanol, t-butanol, and 1,4-butanediol. The hydrogenation catalyst is selected appropriately from known ones that have been used for hydrogenation reaction, such as those mainly comprising cobalt, nickel, palladium, platinum, ruthenium, or rhodium. Solvents that can be used in the reaction generally include alkanols having 1 to 6 carbon atoms, water, tertiary amines, and ethers having 2 to 10 carbon atoms. If desired, hydrolysis of the ester with an acid catalyst or hydrolysis of the acetal can be performed in an arbitrary stage.

After the reduction and amination reaction, the catalyst and ammonia are separated from the reaction product, and, if necessary, the 6-aminocaproic acid is isolated and further purified to recover as a product. In the preparation of e-caprolactam, the aminocaproic acid-containing solution after separation of the catalyst and ammonia or the aminocaproic acid obtained by the isolation and purification operations is condensed and cyclized by heating usually to 100 to 370° C. to obtain the desired product. e-caprolactam is separated and recovered from the reaction product by common means such as distillation.

It is possible to obtain adipic acid as a main product by making slight alterations to the reaction conditions of the process according to the present invention. In this case, too, the source of molecular oxygen can be pure oxygen or diluted oxygen such as air. The same gases as used in the preparation of adipaldehyde-acid can be used as a diluent gas. While the gas can have atmospheric pressure or can be pressurized, it is desirable that the oxygen partial pressure be slightly higher than that used in producing adipaldehyde-acid as a main product. Specifically, it is desirable that the oxygen partial pressure be maintained in a range of from 0.05 to 2.5 MPa, preferably 0.07 to 1.5 MPa, still preferably 0.09 to 0.8 MPa, from beginning to end of the reaction. The term "beginning" means the stage when all the substances necessary for the reaction are in a reactor. Where the reaction is at temperatures higher than room temperature, the term means the stage when the mixture of the substances necessary for the reaction reaches the temperature necessary for the reaction. The term "end" of the reaction means a stage after the beginning of the reaction, in which stage the composition of the substances necessary for the reaction (including the oxygen partial pressure) is out of separately specified conditions or, in which stage the temperature is lower than the one necessary for the reaction by 30° C. or more.

The process of the present invention will now be illustrated in greater detail with reference to Examples and Reference Examples, but the present invention is not construed as being limited thereto unless modifications added thereto deviate from the gist of the invention.

The acid amount of a catalyst was obtained by acidimetry under the following conditions.

The catalyst is dried at 120° C. in air under atmospheric pressure for 12 hours. The dried sample (catalyst) is allowed to cool to room temperature in a desiccator. A 0.25 g portion is weighed out of the dried sample, put into an eggplant type flask (25 ml), and cooled on an ice bath. To the flask is added 4.25 ml of a 4.3N sodium chloride aqueous solution cooled to 0° C., followed by stirring for 10 minutes while maintaining at 0° C. The mixture is filtered through a polyether sulfone membrane having an average pore size of 0.8 μm. The filtrate is neutralization-titrated with a 0.02N sodium hydroxide aqueous solution. The acid equivalent thus determined is divided by the weight of zeolite to obtain an acid amount per unit weight of zeolite (unit: mmol/g).

REFERENCE EXAMPLES

Preparation of Fixed Catalysts

Reference Example 1 (Fixed catalyst-1)

A solution of 8.33 g of iron (II) sulfate heptahydrate in 150 ml of water was added to 16.00 g of FAU type zeolite HSZ-360HUA available from Tosoh Corp. (2Si/Al=14.0 (representing the quotient of the mole number of Si divided by a half of the mole number of Al; hereinafter the same), $Na_2O/SiO_2$=0.0008 (by molar ratio), H type). The mixture was stirred at room temperature for 3 hours in an inert gas atmosphere. The resulting solid (sample) was washed with water and dried. X-Ray fluorometry (hereinafter abbreviated as XRF) revealed that the iron content of the sample was 0.35% in terms of weight concentration.

A part of the sample was taken out and dried at 120° C. under reduced pressure (3 kPa) for 3 hours. It weighed 4.30 g. 2,2'-Bipyridyl weighing 0.0417 g (which was about equivalent to iron in the sample) was added thereto, followed by thorough shaking. The pressure was reduced to 3 kPa, under which the mixture was maintained at room temperature for 1 hour and then at 120° C. for 3 hours. Subsequently, 0.0496 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 3 hours to obtain (fixed catalyst-1).

Reference Example 2 (Fixed catalyst-2)

A solution of 8.98 g of iron (III) nitrate nonahydrate in 221 ml of 0.1M nitric acid was added to 23.6 g of FAU type zeolite CBV-760 available from PQ Corp. (2Si/Al=55.0 (by molar ratio), H type), and the mixture was stirred at room temperature for 1 hour in an air atmosphere. The resulting solid (sample) was washed with water and dried. XRF revealed that the iron content of the sample was 0.50% in terms of weight concentration.

A part of the sample was taken out and dried at 120° C. under reduced pressure of 3 kPa for 3 hours. It weighed 20.02 g. 2,2'-Bipyridyl weighing 0.268 g (which was about equivalent to iron in the sample) was added thereto, followed by thorough shaking. The pressure was reduced to 3 kPa, under which the mixture was maintained at room temperature for 1 hour and then at 120° C. for 3 hours. Subsequently, 0.320 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 200 ml of methylene chloride and washed for 1 hour under reflux condition, followed by filtration. The washing operation was conducted twice. The sample was dried at 60° C. under reduced pressure of 3 kPa for 3 hours to obtain (fixed catalyst-2).

Reference Example 3 (Fixed catalyst-3)

A solution of 3.02 g of iron (III) nitrate nonahydrate in 150 ml of 0.1M nitric acid was added to 16.00 g of FAU type zeolite HSZ-360HUA available from Tosoh Corp. (2Si/Al= 14.0 (by molar ratio), $Na_2O/SiO_2$=0.0008 (by molar ratio), H type), and the mixture was stirred at room temperature for 1 hour in an air atmosphere. The resulting solid (sample) was washed with water and dried. XRF revealed that the iron content of the sample was 0.78% in terms of weight concentration.

A part of the sample was taken out and dried at 120° C. under reduced pressure of 3 kPa for 3 hours. It weighed 2.53 g. 2,2'-Bipyridyl weighing 0.0549 g (which was about equivalent to iron in the sample) was added thereto, followed by thorough shaking. The pressure was reduced to 3 kPa, under which the mixture was maintained at room temperature for 1 hour and then at 120° C. for 3 hours. Subsequently, 0.0656 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition, followed by filtration. The washing operation was conducted twice. The sample was dried at 60° C. under reduced pressure of 3 kPa for 3 hours to obtain (fixed catalyst-3).

Reference Example 4 (Fixed catalyst-4)

To 2.14 g of (fixed catalyst-3) was added 30 ml of a 2M aqueous solution of sodium nitrate, and the mixture was treated under reflux condition for 2 hours, followed by filtration and washing with water. The sodium ion-exchanging treatment was conducted once more. The sample was washed with desalted water and dried at 60° C. under reduced pressure of 3 kPa for 5 hours to obtain (fixed catalyst-4). The resulting (fixed catalyst-4) was found by XRF to have an iron content of 0.70% in terms of weight concentration. The Na/Al (by molar ratio) was 0.085.

Reference Example 5 (Fixed catalyst-5)

A solution of 3.02 g of iron (III) nitrate nonahydrate in 150 ml of 0.1M nitric acid was added to 16.00 g of FAU type zeolite HSZ-360HUA available from Tosoh Corp. (2Si/Al= 14.0 (by molar ratio), $Na_2O/SiO_2$=0.0008 (by molar ratio), H type), and the mixture was stirred at room temperature for 1 hour in an air atmosphere. The resulting solid (sample) was washed with water and dried.

A 5.00 g portion of the dried sample was added to 47 ml of a 2M sodium nitrate aqueous solution and treated under reflux condition for 2 hours, followed by filtration and washing with water. The sodium ion-exchanging treatment was performed twice more (three times in total). The sample was washed with desalted water and dried at 120° C. for 12 hours under atmospheric pressure in air. The iron content of the sample as measured by XRF was 0.76% in terms of weight concentration. The Na/Al (by molar ratio) was found to be 0.18.

A part of the sample was taken out and dried at 100° C. under reduced pressure of 3 kPa for 3 hours. It weighed 1.04 g. 2,2'-Bipyridyl weighing 0.0226 g (which was about equivalent to iron in the sample) was added thereto, followed by thorough shaking. The pressure was reduced to 3 kPa, under which the mixture was maintained at room temperature for 1 hour and then at 120° C. for 3 hours. Subsequently, 0.0264 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 30 ml of methylene chloride and washed under reflux condition for 1 hour, followed by filtration. The washing operation was conducted twice. The sample was dried at 60° C. under reduced pressure of 3 kPa for 3 hours to obtain (fixed catalyst-5).

Reference Example 6 (Fixed catalyst-6)

A solution of 33.40 g of iron (II) sulfate heptahydrate and 0.6 ml of 1M hydrochloric acid in 600 ml of water was added to 64.0 g of FAU type zeolite CBV-760 available from PQ Corp. (2Si/Al=55.0 (by molar ratio), H type), and the mixture was stirred at room temperature for 3 hours in an inert gas atmosphere. The resulting solid (sample) was washed with water and dried. XRF revealed that the iron content of the sample was 0.47% in terms of weight concentration (designated (fixed catalyst-6)).

Reference Example 7 (Fixed catalyst-7)

To 4.00 g of (fixed catalyst-6) was added 25 ml of water, and 7.15 ml of 0.1M aqueous ammonia was further added thereto. The resulting slurry was stirred at room temperature for 10 minutes, followed by filtration. The solid was washed with desalted water until the pH of the filtrate was reduced to 7.5. The sample was dried under reduced pressure in an evaporator to obtain (fixed catalyst-7).

Reference Example 8 (Fixed catalyst-8)

(Fixed catalyst-7) was heat treated at 510° C. for 4 hours in a nitrogen stream to obtain (fixed catalyst-8).

Reference Example 9 (Fixed catalyst-9)

In a mixture of 40 ml of water and 20 ml of methanol was dissolved 0.541 g of iron (III) chloride hexahydrate, and 0.164 g of sodium hydrogencarbonate, 0.313 g of 2,2'-bipyridyl, and 0.373 g of 2,2'-biphenyldiol were added to the solution in the order described. The mixture was stirred at room temperature to obtain a dark red mixture. To the mixture were added 29.4 g of 1-butanol, 83.4 g of ethyl silicate, and 3.31 g of dodecatungstosilicic acid hexacosahydrate. The resulting slurry was stirred at 45° C. for 1 hour and then at 80° C. for 4 hours and 45 minutes, followed by aging at room temperature for 15 hours. The resulting gelled sample was evaporated under reduced pressure to remove the solvent. The resulting deep red dry gel was washed with water at 80° C. three times and dried in an air atmosphere at 120° C. for 12 hours to obtain (fixed catalyst-9).

When (fixed catalyst-9) was fired at 600° C. for 6 hours in an air stream, the weight loss was 24%. The resulting yellowish white powder was found to have an iron content of 0.16% in terms of weight concentration by XRF. Accordingly, (fixed catalyst-9) was considered to have an iron content of 0.12%.

Reference Example 10 (Fixed catalyst-10)

To a solution of 4.05 g of iron (III) nitrate nonahydrate in 100 ml of water was added 10.0 g of a silica type catalyst carrier (CARiACT Q-15 available from Fuji Silysia Co., Ltd.; particle size: 75 to 500 μm; pore size: about 150). Immediately thereafter 2.02 ml of concentrated (28 to 30 wt %) aqueous ammonia was added dropwise. The resulting slurry was stirred at 60° C. for 1 hour, followed by filtration. The cake was washed with desalted water until the pH of the filtrate was lowered to about 7. The filtered sample was dried under reduced pressure in an evaporator and then heat treated at 600° C. for 4 hours in a nitrogen stream to obtain yellowish white powder (designated (fixed catalyst-10)).

Each of the fixed catalysts obtained in Reference Examples 1 to 10 was analyzed by acidimetry according to the method described above to calculate an acid amount. The results obtained are shown in Table 1 below.

TABLE 1

| Fixed Catalyst | Acid Amount (mmol/g) |
|---|---|
| 1 | 0.087 |
| 2 | 0.085 |
| 3 | 0.058 |
| 4 | 0.015 |
| 5 | 0.035 |
| 6 | 0.175 |
| 7 | 0.020 |
| 8 | 0.141 |
| 9 | 0.016 |
| 10 | 0.016 |

Example 1

Oxidative Ring Cleavage of Cyclohexanone With (fixed catalyst-1)

In a glass-made reactor having an inner diameter of 50 mm and an inner height of 25 mm were put 1.79 g of (fixed catalyst-1), 15 ml of water, and 1.5 g of cyclohexanone and allowed to react at 65° C. for 1.5 hours with molecular oxygen added to increase the pressure slightly (about 1 kPa over atmospheric pressure) while stirring with an almost cylindrical Teflon-coated stirrer bar having a full length of 30 mm and a maximum diameter of 8 mm by means of a magnetic stirrer at 1200 to 1500 rpm. The fixed catalyst was removed from the resulting reaction mixture by centrifugation, and the liquid phase was extracted with a solvent (methanol). The extract was analyzed by gas chromatography using an internal standard to find that the yield of adipaldehyde-acid, the desired product, was 0.96%.

Analysis of (fixed catalyst-1) After Reaction

After the reaction, 1.77 g of (fixed catalyst-1) was recovered (99% of the charged amount). Elementary analysis on the recovered catalyst by XRF revealed a 1% increase of 2Si/Al (by molar ratio), a change of Fe/Al (by molar ratio) of not more than the detection limit (1%), and a 3% decrease of the Fe content. Powder X-ray diffractometry detected no change in crystallinity due to the reaction (not more than the detection limit, 1%).

Examples 2 to 5 and Comparative Examples 1 to 6

Oxidative ring cleavage of cyclohexanone was carried out under the same reaction conditions as in Example 1 to obtain adipaldehyde-acid, the desired product, except that the amount of the fixed catalyst and the reaction temperature were changed as shown in Table 2. The reaction results are shown in Table 2.

TABLE 2

| | Fixed Catalyst | Amount of Catalyst (g) | Reaction Temp. (° C.) | Adipaldehyde-acid Yield (%) |
|---|---|---|---|---|
| Example 2 | catalyst-2 | 1.29 | 65 | 1.59 |
| Example 3 | catalyst-2 | 1.29 | 85 | 3.5 |
| Example 4 | catalyst-6 | 2.00 | 85 | 6.2 |
| Example 5 | catalyst-8 | 2.00 | 85 | 4.7 |
| Compar. Example 1 | catalyst-3 | 0.520 | 65 | 0.28 |
| Compar. Example 2 | catalyst-4 | 0.573 | 65 | 0.48 |
| Compar. Example 3 | catalyst-5 | 0.524 | 65 | (−) |
| Compar. Example 4 | catalyst-7 | 2.00 | 85 | 0.14 |
| Compar. Example 5 | catalyst-9 | 1.40 | 65 | 0.15 |
| Compar. Example 6 | catalyst-10 | 2.00 | 85 | (−) |

(−): not obtained.

Comparative Example 7

A reaction carried out under the same conditions as in Example 1 except for using 2.00 g of (fixed catalyst-1) and replacing molecular oxygen with a nitrogen gas flow failed to produce adipaldehyde-acid, the desired product.

Comparative Example 8

A reaction carried out under the same conditions as in Example 1, except for using 2.00 g of FAU type zeolite CBV-760 available from PQ Corp. (2Si/Al=55.0 (by molar ratio), H type), failed to produce adipaldehyde-acid, the desired product.

Reference Examples

Preparation of Fixed Catalysts (heat treated)

Reference Example 11 (Iron-on-FAU zeolite-1)

A solution of 16.7 g of iron (II) sulfate heptahydrate in 300 ml of water the pH of which had been adjusted to 4 with hydrochloric acid was added to 32.00 g of FAU type zeolite CBV-760 available from PQ Corp. (2Si/Al=55.0 (by molar ratio), H type), and the mixture was stirred at room temperature for 3 hours in an inert gas atmosphere. The resulting solid (sample) was washed with water and dried. X-ray fluorometry (hereinafter abbreviated as XRF) revealed that the iron content of the sample was 0.47% in terms of weight concentration. The 2Si/Al (by molar ratio) after the Fe ion exchange was 67.

Reference Example 12 (Fixed catalyst-11)

A part of (iron-on-FAU zeolite-1) was taken out and dried at 120° C. under reduced pressure of 3 kPa for 3 hours. It weighed 2.83 g. To the sample was added 0.0377 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Subsequently, 0.0449 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 3 hours to obtain (fixed catalyst-11).

Reference Example 13 (Fixed catalyst-12)

A part of (iron-on-FAU zeolite-1) was taken out and heat treated in a tubular furnace at 400° C. for 24 hours in a nitrogen stream. XRF on the fired sample revealed no significant difference in iron content from (iron-on-FAU zeolite-1).

A part of the sample was taken out. It weighed 2.38 g immediately after the heat treatment. To the sample was added 0.031 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Subsequently, 0.038 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 2 hours to obtain (fixed catalyst-12).

Reference Example 14 (Fixed-Catalyst 13)

A part of (iron-on-FAU zeolite-1) was taken out and heat treated in a tubular furnace at 740° C. for 4 hours in a nitrogen stream.

A part of the sample was taken out. It weighed 2.50 g immediately after the heat treatment. To the sample was added 0.033 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Subsequently, 0.039 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 2 hours to obtain (fixed catalyst-13).

Reference Example 15 (Fixed-Catalyst 14)

A part of (iron-on-FAU zeolite-1) was taken out and heat treated in a tubular furnace at 900° C. for 4 hours in a nitrogen stream. The iron content of the fired sample was found to be 0.53% in terms of weight concentration by XRF.

A part of the sample was taken out. It weighed 4.07 g immediately after the heat treatment. To the sample was added 0.060 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Subsequently, 0.072 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 2 hours to obtain (fixed catalyst-14).

Reference Example 16 (Fixed-catalyst 15)

A part of (iron-on-FAU zeolite-1) was taken out and heat treated in a tubular furnace at 900° C. for 4 hours in an air stream.

A part of the sample was taken out. It weighed 2.59 g immediately after the heat treatment. To the sample was added 0.034 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Subsequently, 0.041 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 2 hours to obtain (fixed catalyst-15).

Reference Example 17 (Fixed catalyst-16)

A solution of 33.4 g of iron (II) sulfate heptahydrate in 600 ml of water the pH of which had been adjusted to 4 with hydrochloric acid was added to 64.0 g of FAU type zeolite CBV-760 available from PQ Corp. (2Si/Al=55.0 (by molar ratio), H type), and the mixture was stirred at room temperature for 3 hours in an inert gas atmosphere. The resulting solid (sample) was washed with water and dried. XRF revealed that the iron content of the sample was 0.46% in terms of weight concentration. The 2Si/Al (by molar ratio) after the Fe ion exchange was 66.

A part of the sample was taken out and heat treated in a tubular furnace at 750° C. for 4 hours in a nitrogen stream.

A part of the heat-treated sample was taken out. It weighed 49.72 g immediately after the heat treatment. To the sample was added 0.645 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Subsequently, 0.763 g of 2,2'-biphenyldiol (which was about equivalent to iron in the sample) was added thereto, followed by thorough shaking. The pressure was reduced to 3 kPa, under which the mixture was kept at room temperature for 1 hour and then at 120° C. for 3 hours. The resulting sample was poured into 500 ml of methylene chloride and washed for 1 hour under reflux condition, followed by filtration. The washing operation was conducted twice. The sample was dried at 60° C. under reduced pressure of 3 kPa for 2 hours to obtain (fixed catalyst-16).

Reference Example 18 (Iron-on-FAU Zeolite-2)

A solution of 33.4 g of iron (II) sulfate heptahydrate in 600 ml of water the pH of which had been adjusted to 4 with hydrochloric acid was added to 64.0 g of FAU type zeolite CBV-760 available from PQ Corp. (2Si/Al=55.0 (by molar ratio), H type), and the mixture was stirred at room temperature for 3 hours in an inert gas atmosphere. The resulting solid (sample) was washed with water and dried. XRF revealed that the iron content of the sample was 0.47% in terms of weight concentration. The 2Si/Al (by molar ratio) after the Fe ion exchange was 66.

A part of the sample was taken out and heat treated in a tubular furnace at 750° C. for 4 hours in a nitrogen stream to obtain (iron-on-FAU zeolite-2).

Reference Example 19 (Fixed Catalyst-17)

A 4.10 g portion of the (iron-on-FAU zeolite-2) was taken out, and 0.062 g of 1,10-phenanthroline.monohydrate (which was about equivalent to iron in the sample) followed by thorough shaking. The pressure was reduced to 3 kPa, under which the mixture was maintained at room temperature for 1 hour and then at 120° C. for 3 hours. The resulting sample was poured into 100 ml of methylene chloride and washed for 1 hour under reflux condition, followed by filtration. The washing operation was conducted twice. The sample was dried at 60° C. under reduced pressure of 3 kPa for 2 hours to obtain (fixed catalyst-17).

Reference Example 20 (Fixed Catalyst-18)

A 2.93 g portion of the (iron-on-FAU zeolite-2) was taken out, and 0.0317 g of acetylacetone (which was about 1.2 equivalent to iron in the sample) followed by thorough shaking. The pressure was reduced to 3 kPa, under which the mixture was maintained at 120° C. for 3 hours. The resulting sample was poured into 50 ml of methylene chloride and washed for 1 hour under reflux condition and filtered. The washing operation was conducted twice. The sample was dried at 60° C. under reduced pressure of 3 kPa for 2 hours to obtain (fixed catalyst-18).

Reference Example 21 (Fixed Catalyst-19)

FAU type zeolite CBV-760 available from PQ Corp. (2Si/Al=55.0 (by molar ratio), H type) was heat treated in a tubular furnace at 750° C. for 4 hours in a nitrogen stream. A solution of 33.4 g of iron (II) sulfate heptahydrate in 600 ml of water the pH of which had been adjusted to 4 with hydrochloric acid was added to 8.00 g of the heat-treated sample, and the mixture was stirred at room temperature for 3 hours in an inert gas atmosphere. The resulting sample was washed with water and dried. XRF revealed that the iron content of the sample was 0.52% in terms of weight concentration. The 2Si/Al (by molar ratio) after the Fe ion exchange was 67.

A part of the sample was taken out and dried under reduced pressure of about 3 kPa at 120° C. for 3 hours. After the drying, it weighed 3.05 g. To the sample was added 0.045 g of 2,2'-bipyridyl (which was about equivalent to iron in the sample) followed by thorough shaking. The pressure was reduced to 3 kPa, under which the mixture was maintained at room temperature for 1 hour and then at 120° C. for 3 hours. Then, 0.053 g of 2,2'-biphenyldiol (which was about equivalent to iron in the sample) was added thereto, followed by thorough shaking. The pressure was reduced to 3 kPa, under which the mixture was maintained at room temperature for 1 hour and then at 120° C. for 3 hours. The resulting sample was poured into 50 ml of methylene chloride and washed for 1 hour under reflux condition, followed by filtration. The washing operation was conducted twice. The sample was dried at 60° C. under reduced pressure of 3 kPa for 3 hours to obtain (fixed catalyst-19).

Example 6

In a glass-made reactor having an inner diameter of 50 mm and an inner height of 25 mm were put 2.00 g of (fixed catalyst-12), 15 ml of water, and 1.5 g of cyclohexanone and allowed to react at 85° C. for 1.5 hours with molecular oxygen added to increase the pressure slightly (about 1 kPa over atmospheric pressure) while stirring with an almost cylindrical Teflon-coated stirrer bar having a full length of 30 mm and a maximum diameter of 8 mm by means of a magnetic stirrer at 1200 to 1500 rpm. The fixed catalyst was removed from the resulting reaction mixture by centrifugation, and the liquid phase was extracted with a solvent (methanol). The extract was analyzed by gas chromatography using an internal standard to find that the yield of adipaldehyde-acid, the desired product, was 5.54%.

Example 7

Oxidative ring cleavage of cyclohexanone was carried out under the same reaction conditions as in Example 6, except for using 2.00 g of (fixed catalyst-13). As a result, adipaldehyde-acid, the desired compound, was obtained in a yield of 5.70%.

Example 8

Oxidative ring cleavage of cyclohexanone was carried out under the same reaction conditions as in Example 6, except for using 2.00 g of (fixed catalyst-14). As a result, adipaldehyde-acid, the desired compound, was obtained in a yield of 6.60%.

Example 9

Oxidative ring cleavage of cyclohexanone was carried out under the same reaction conditions as in Example 6, except for using 2.00 g of (fixed catalyst-15). As a result, adipaldehyde-acid, the desired compound, was obtained in a yield of 6.44%.

Example 10

In a 500 ml-volume autoclave made of titanium were put 10.0 g of (fixed catalyst-16), 75.0 g of water, and 7.49 g of cyclohexanone. A mixed gas of oxygen 5% and nitrogen 95% (in terms of volume concentration) was fed into the reaction mixture from a gas inlet equipped with an outlet and made to flow to a cooling tube fitted to the top of the autoclave at a flow rate of 10 Nl/hr while maintaining the inner pressure at 0.1 MPa, and the reaction mixture was allowed to react at 85° C. for 1.5 hours while agitating with a 6-bladed turbine at 1000 rpm. The fixed catalyst was separated from the reaction mixture by centrifugation, and the liquid phase was extracted with a solvent (methanol). The extract was analyzed by gas chromatography using an internal standard to find that the yield of adipaldehyde-acid, the desired product, was 8.8%.

Example 11

Oxidative ring cleavage of cyclohexanone was carried out under the same reaction conditions as in Example 10, except that 20.0 g of (fixed catalyst-16) was used and that a mixed gas of oxygen 5% and nitrogen 95% (in terms of volume concentration) was made to flow at a rate of 18 Nl/hr. As a result, adipaldehyde-acid, the desired compound, was obtained in a yield of 9.9%. The yield of adipic acid was 1.88%.

Example 12

Oxidative ring cleavage of cyclohexanone was carried out under the same reaction conditions as in Example 6, except for using 2.00 g of (fixed catalyst-17). As a result, adipaldehyde-acid, the desired compound, was obtained in a yield of 6.60%.

Example 13

Oxidative ring cleavage of cyclohexanone was carried out under the same reaction conditions as in Example 6, except for using 2.00 g of (fixed catalyst-18). As a result, adipaldehyde-acid, the desired compound, was obtained in a yield of 5.24%.

Example 14

Oxidative ring cleavage of cyclohexanone was carried out under the same reaction conditions as in Example 6, except for using 2.00 g of (fixed catalyst-19). As a result, adipaldehyde-acid, the desired compound, was obtained in a yield of 5.53%.

Example 15

Oxidative ring cleavage of cyclohexanone was carried out under the same reaction conditions as in Example 6, except for using 2.00 g of (fixed catalyst-11). As a result, adipaldehyde-acid, the desired compound, was obtained in a yield of 4.58%.

Reference Examples

Preparation of Fixed Catalysts (with basic compound added)

Reference Example 22 (Fixed catalyst-20)

A solution of 4.05 g of iron (III) nitrate nonahydrate in 100 ml of desalted water was added to 10.00 g of FAU type zeolite CBV-760 available from PQ Corp. (2Si/Al=55.0 (by molar ratio), H type), and the mixture was stirred at room temperature for 1 minute in an air atmosphere. To the resulting slurry was added dropwise 1.82 ml of concentrated (28 to 30 wt %) aqueous ammonia ($NH_3$/Fe (molar ratio to iron element added): 2.79) over 5 minutes while keeping the slurry at room temperature. The resulting yellowish brown slurry was heated to 60° C., at which it was stirred for 1 hour. The sample was collected by filtration and washed with desalted water until the pH of the filtrate was lowered to 7.5 or less. The sample was dried under reduced pressure in an evaporator and then treated in a tubular furnace at 750° C. for 3 hours in a nitrogen stream. The resulting sample was designated (fixed catalyst-1).

The resulting solid (sample) was washed with water and dried. The iron content was found to be 1.25% in terms of weight percent concentration by X-ray fluorometry (hereinafter abbreviated as XRF). The 2Si/Al (by molar ratio) after Fe supporting was 68.

Reference Example 23 (Fixed catalyst-21)

Fixed catalyst-21 was prepared in the same manner as in Reference Example 22 (for (fixed catalyst-20)), except that the volume of the concentrated aqueous ammonia added in the Fe supporting stage was changed to 3.04 ml ($NH_3$/Fe (by molar ratio): 4.66). The iron content as analyzed by XRF was 4.84%.

Reference Example 24 (Fixed catalyst-22)

To a solution of 4.05 g of iron (III) nitrate nonahydrate in 100 ml of desalted water was added dropwise 1.82 ml of concentrated (28 to 30 wt %) aqueous ammonia over 5 minutes while stirring the solution at room temperature. The resulting reddish brown reaction mixture was further stirred at room temperature for an additional 30 minute period. Then, 10.00 g of FAU type zeolite CBV-760 available from PQ Corp. (2Si/Al=55.0 (by molar ratio), H type) was put into the mixture, and the temperature was raised to 60° C., at which the mixture was stirred for 1 hour. The sample was collected by filtration and washed with desalted water until the pH of the filtrate was lowered to 7.5 or less. The sample was dried under reduced pressure in an evaporator and then treated in a tubular furnace at 750° C. for 3 hours in a nitrogen stream. The resulting sample was designated (fixed catalyst-22).

The resulting solid (sample) was washed with water and dried. The iron content of the sample was found by XRF to be 0.91% in terms of weight percent concentration.

Reference Example 25 (Fixed catalyst-23)

A solution of 4.05 g of iron (III) nitrate nonahydrate in 100 ml of desalted water was added to 10.00 g of FAU type zeolite CBV-760 available from PQ Corp. (2Si/Al=55.0 (by molar ratio), H type), and the temperature was raised up to 60° C. in an air atmosphere, at which the mixture was stirred for 30 minutes. To the reaction mixture was added dropwise 1.82 ml of concentrated (28 to 30 wt %) aqueous ammonia over 5 minutes while stirring at 60° C. The resulting yellowish brown slurry was further stirred at 60° C. for 30 minutes. The sample was collected by filtration and washed with desalted water until the pH of the filtrate was lowered to 7.5 or less. The sample was dried under reduced pressure in an evaporator and then treated in a tubular furnace at 750° C. for 3 hours in a nitrogen stream. The resulting sample was designated (fixed catalyst-23).

The resulting solid (sample) was washed with water and dried. The iron content was found by XRF to be 1.55% in terms of weight percent concentration.

Reference Example 26 (Fixed catalyst-24)

A solution of 4.04 g of iron (III) nitrate nonahydrate in 100 ml of desalted water was added to 10.00 g of FAU type zeolite CBV-760 available from PQ Corp. (2Si/Al=55.0 (by molar ratio), H type), and the temperature was raised up to 60° C. in an air atmosphere, at which the mixture was stirred for 55 minutes. To the reaction mixture was added dropwise 1.82 ml of concentrated (28 to 30 wt %) aqueous ammonia over 5 minutes while stirring at 60° C. The resulting yellowish brown slurry was further stirred at 60° C. for 5 minutes. The sample was collected by filtration and washed with desalted water until the pH of the filtrate was lowered to 7.5 or less. The sample was dried under reduced pressure in an evaporator and then treated in a tubular furnace at 750° C. for 3 hours in a nitrogen stream. The resulting sample was designated (fixed catalyst-24).

The resulting solid (sample) was washed with water and dried. The iron content was found by XRF to be 1.49% in terms of weight percent concentration.

Reference Example 27 (Fixed Catalyst-25)

To 30.0 g of FAU type zeolite CBV-760 available from Zeolyst International (2Si/Al=55.0 (by molar ratio); H type) was added 600 ml of a 1 mol/l aqueous solution of ammonium nitrate, followed by stirring at 80° C. for 1 hour. The sample was collected by filtration and washed with desalted water. To the sample was again added 600 ml of a 1 mol/l ammonium nitrate aqueous solution, and the mixture was stirred at 80° C. for 1 hour, followed by filtration, washing and drying to obtain ammonium type FAU zeolite.

A 10.00 g portion of the resulting ammonium type FAU zeolite was added a solution of 4.05 g of iron (III) nitrate nonahydrate in 100 ml of desalted water, and the temperature was raised up to 60° C. in an air atmosphere, at which the mixture was stirred for 30 minutes. To the reaction mixture was added dropwise 1.82 ml of concentrated (28 to 30 wt %) aqueous ammonia over 5 minutes while stirring at 60° C. The resulting yellowish brown slurry was further stirred at 60° C. for 30 minutes. The sample was collected by filtration and washed with desalted water until the pH of the filtrate was lowered to 7.5 or less. The sample was dried under reduced pressure in an evaporator and then treated in a tubular furnace at 750° C. for 3 hours in a nitrogen stream. The resulting sample was designated (fixed catalyst-25).

The resulting solid (sample) was washed with water and dried. The iron content was found by XRF to be 1.63% in terms of weight percent concentration.

Reference Example 28 (Fixed Catalyst-26)

A solution of 4.05 g of iron (III) nitrate nonahydrate in 100 ml of desalted water was added to 10.00 g of FAU type zeolite CBV-760 from PQ Corp. (2Si/Al=55.0 (by molar ratio), H type), and the temperature was raised up to 60° C., at which the mixture was stirred for 1 hour. The sample was collected by filtration and washed with desalted water until the pH of the filtrate was lowered to 6.5 or less. The sample was dried under reduced pressure in an evaporator and then treated in a tubular furnace at 750° C. for 3 hours in a nitrogen stream. The resulting sample was designated (fixed catalyst-26).

The resulting solid (sample) was washed with water and dried. The iron content was found by XRF to be 0.77% in terms of weight percent concentration. The 2Si/Al (by molar ratio) after the Fe ion exchange was 70.

Reference Example 29 (Fixed catalyst-27)
(preparation of ammonium type zeolite)

To 30.00 g of FAU type zeolite CBV-760 from PQ Corp. (2Si/Al=55.0 (by molar ratio), H type) was added 600 ml of a 1N ammonium nitrate aqueous solution, and the mixture was stirred at 80° C. for 1 hour. The sample was filtered and washed. The above procedure was conducted twice. The sample was dried at 120° C. for 12 hours to obtain ammonium type zeolite.

To a 12.0 g portion of the resulting ammonium type zeolite was added a solution of 4.85 g of iron (II) nitrate nonahydrate in 120 ml of desalted water, and the mixture was stirred at 60° C. for 30 minutes in an air atmosphere. To the resulting slurry was added dropwise 2.18 ml of concentrated (28 to 30 wt %) aqueous ammonia over 5 minutes. The resulting yellowish brown slurry was further stirred at 60° C. for 30 minutes. The sample was collected by filtration and washed with desalted water until the pH of the filtrate was lowered to 7.5 or less. The sample was dried under atmospheric pressure at 120° C. for 12 hours. The above operation for iron supporting was conducted three times for the same catalyst.

The resulting sample was treated in a tubular furnace at 750° C. for 3 hours in a nitrogen stream. The resulting sample was designated (fixed catalyst-27).

Example 16

In a glass-made reactor having an inner diameter of 50 mm and an inner height of 25 mm were put 2.00 g of (fixed catalyst-20), 15 ml of water, and 1.5 g of cyclohexanone and allowed to react at 85° C. for 1.5 hours with molecular oxygen added to increase the pressure slightly (about 1 kPa over atmospheric pressure) while stirring with an almost cylindrical Teflon-coated stirrer bar having a full length of 30 mm and a maximum diameter of 8 mm by means of a magnetic stirrer at 1200 to 1500 rpm. The fixed catalyst was removed from the reaction mixture by centrifugation, and the liquid phase was extracted with a solvent (methanol). The extract was analyzed by gas chromatography using an internal standard to find that the yield of adipaldehyde-acid, the desired product, was 7.4%.

Examples 17 to 23

Oxidative ring cleavage of cyclohexanone was carried out in the same manner as in Example 15, except for using 2.00 g of each of (fixed catalyst-21) to (fixed catalyst-27), to obtain adipaldehyde-acid as a desired product. The reaction results are shown in Table 3.

TABLE 3

|  | Catalyst | Adipaldehyde-acid Yield |
| --- | --- | --- |
| Example 17 | fixed catalyst-21 | 7.9% |
| Example 18 | fixed catalyst-22 | 7.4% |
| Example 19 | fixed catalyst-23 | 8.5% |
| Example 20 | fixed catalyst-24 | 8.0% |
| Example 21 | fixed catalyst-25 | 7.1% |
| Example 22 | fixed catalyst-26 | 6.7% |
| Example 23 | fixed catalyst-27 | 9.3% |

Adipic acid was produced in a yield of 1.46% in Example 18 (with (fixed catalyst-22)) and 1.39% in Example 19 (with (fixed catalyst-23)).

INDUSTRIAL APPLICABILITY

The present invention makes it possible to use a fixed catalyst which comprises a carrier having supported thereon a specific metal element and has specific properties as a catalyst for oxidative ring cleavage in an oxidation reaction of a cyclic ketone, especially in the production of adipaldehyde-acid from cyclohexanone. As a result, the steps for catalyst separation and for product purification can be simplified, and a system free of halogen as a counter ion can be established, which allows use of lower grade materials for reactors and the like. Accordingly, the present invention bring us great industrial benefits.

What is claimed is:

1. A process for producing an aliphatic aldehyde-acid and/or aliphatic dicarboxylic acids comprising:
   oxidizing a cyclic ketone with molecular oxygen in the presence of a fixed bed catalyst, wherein said catalyst comprises a carrier selected from the group consisting of a clay and a metal oxide and at least one metal belonging to Groups 4–11 of the Periodic Table, said metal being supported on said carrier, wherein said catalyst has an acid amount of at least 0.06 mmol/g per unit weight of said carrier.

2. The process according to claim 1, wherein said metal oxide carrier is a zeolite.

3. The process according to claim 1, wherein said cyclic ketone is cyclohexanone, said aliphatic aldehyde-acid is adipaldehyde-acid, and said aliphatic dicarboxylic acid is adipic acid.

4. The process according to claim 2, wherein said metal element belonging to groups 4 to 11 of the Periodic Table is selected from the group consisting of iron, copper and iridium.

5. The process according to claim 4, wherein said metal element is iron

6. The process according to claim 2, wherein said metal element supported on a zeolite is an iron ion and or iron complex.

7. The process according to claim 2, wherein said composite includes elements constituting a skeleton of said zeolite, wherein the molar ratio of said elements is 8 or greater after supporting the metal element, where a proportion of the elements is represented by the formula 2T/M, wherein T is at least one element selected from the group consisting of silicon, germanium and tin, and M is at least one element selected from the group consisting of aluminum, gallium, indium and boron.

8. The process according claim 2, wherein said zeolite includes elements constituting a skeleton of said zeolite, wherein the molar ratio of said elements is 9 or greater before supporting the metal element, where a proportion of the elements is represented by the formula 2T/M, wherein T is at least one element selected from the group consisting of silicon, germanium and tin, and M is at least one element selected from the group consisting of aluminum, gallium, indium and boron.

9. The process according to claim 7, wherein the element T is silicon.

10. The process according to claim 7, wherein the element M is aluminum.

11. A process for producing e-caprolactam comprising:
oxidizing cyclohexanone with molecular oxygen in the presence of a fixed catalyst, said catalyst comprising a composite of a carrier and at least one metal element belonging to Groups 4 to 11 of the Periodic Table supported on the carrier, said catalyst having an acid amount of 0.06 mmol/g or more per unit weight of said carrier to produce an oxidation product containing adipaldehyde-acid;
reacting the adipaldehyde-acid recovered from the oxidation product with ammonia and hydrogen in the presence of a hydrogenating catalyst to produce 6-aminocaproic acid; and
heating the 6-aminocaproic acid to cause cyclization of the 6-aminocaproic acid into e-caprolactam.

12. The process according to claim 1, further comprising carrying out the oxidation in the presence of water.

13. A process of producing an aliphatic aldehyde-acid and/or an aliphatic dicarboxylic acid comprising:
oxidizing a cyclic ketone with molecular oxygen in the presence of a fixed catalyst, wherein said fixed catalyst comprises a composite of a carrier and at least one metal element belonging to Groups 4 to 11 of the Periodic Table supported on said carrier, said composite includes elements constituting a skeleton of said zeolite, the molar ratio of said elements is 8 or greater after supporting the metal element, where a proportion of the elements is represented by the formula 2T/M, wherein T is at least one element selected from the group consisting of silicon, germanium and tin, and M is at least one element selected from the group consisting of aluminum, gallium, indium and boron.

14. A process of producing an aliphatic aldehyde-acid and/or an aliphatic dicarboxylic acid comprising:
oxidizing a cyclic ketone with molecular oxygen in the presence of a fixed catalyst, wherein said fixed catalyst comprises a composite of zeolite and at least one metal element belonging to Groups 4 to 11 of the Periodic Table supported on said zeolite, said zeolite includes elements constituting a skeleton of said zeolite, the molar ratio of said elements is 9 or greater before supporting the metal element, where a proportion of the elements is represented by the formula 2T/M, wherein T is at least one element selected from the group consisting of silicon, germanium and tin, and M is at least one element selected from the group consisting of aluminum, gallium, indium and boron.

15. The process according to claim 1, wherein said fixed catalyst comprises a carrier having at least one metal element belonging to Groups 4 to 11 of the Periodic Table supported thereon in a liquid phase, further comprising preparing said composite in the presence of a basic compound, said basic compound present in an amount of 0.01 to 50 mol of the basic compound per mole of the total of the metal elements used in the supporting stage.

16. The process according to claim 15, wherein said basic compound is selected from the group consisting of ammonia, a straight-chain alkylamine or an alicyclic alkylamine.

17. The process according to claim 1, further comprising of heat treating the catalyst at a temperature of from 200 to 1100° C.

18. The process according to claim 17, further comprising supporting at least one metal element belonging to groups 4 to 11 of the Periodic Table on the carrier after heat treatment of said carrier.

19. A fixed catalyst for producing an aliphatic aldehyde-acid and/or an aliphatic dicarboxylic acid, comprising a FAU type zeolite and at least one metal element belonging to Groups 4 to 11 of the Periodic Table supported on said FAU type zeolite, said catalyst having an acid amount of 0.06 mmol/g or more per unit weight of said FAU type zeolite.

20. The fixed catalyst according to claim 19, wherein said carrier is zeolite.

21. The fixed catalyst according to claim 19, wherein said metal element belonging to Groups 4 to 11 of the Periodic Table is selected from the group consisting of iron, copper, and iridium.

22. The fixed catalyst according to claim 21, wherein said metal element belonging to groups 4 to 11 of the Periodic Table is iron.

23. The fixed catalyst according to claim 19, wherein said aldehyde-acid is adipaldehyde-acid and said aliphatic dicarboxylic acid is adipic acid.

24. The fixed catalyst according to claim 19, wherein said composite comprises elements constituting a skeleton of said zeolite, wherein the molar ratio of said elements is 8 or greater after supporting the metal element, where the proportion of elements is represented by 2T/M, wherein T is at least one element selected from the group consisting of silicon, germanium and tin, and M is at least one element selected from the group consisting of aluminum, gallium, indium and boron.

25. The fixed catalyst according to claim 20, wherein said zeolite includes elements constituting a skeleton of said zeolite, wherein the molar ratio of said elements is 9 or greater before supporting the metal element, where the proportion of elements is represented by 2T/M, wherein T is at least one element selected from the group consisting of silicon, germanium and tin, and M is at least one element selected from the group consisting of aluminum, gallium, indium and boron.

26. A fixed catalyst for producing an aliphatic aldehyde-acid and/or an aliphatic dicarboxylic acid comprising a composite of zeolite and at least one metal element belonging to Groups 4 to 11 of the Periodic Table supported on said zeolite, wherein said composite includes elements constituting a skeleton of said zeolite, wherein the molar ratio of said elements is 8 or greater after supporting the metal element, where the proportion of elements is represented by 2T/M, wherein T is at least one element selected from the group consisting of silicon, germanium and tin, and M is at least one element selected from the group consisting of aluminum, gallium, indium and boron.

27. A fixed catalyst for producing an aliphatic aldehyde-acid and/or an aliphatic dicarboxylic acid comprising a composite of zeolite and at least one metal element belonging to Groups 4 to 11 of the Periodic Table supported on said zeolite, wherein said composite includes elements constituting a skeleton of said zeolite, wherein the molar ratio of said elements is 9 or greater before supporting the metal element, where the proportion of elements is represented by 2T/M, wherein T is at least one element selected from the group consisting of silicon, germanium and tin, and M is at least one element selected from the group consisting of aluminum, gallium, indium and boron.

28. The fixed catalyst according to claim 20, wherein said fixed catalyst comprises a composite having at least one metal element belonging to Groups 4 to 11 of the Periodic Table supported on the carrier in a liquid phase, said composite being prepared in the presence of a basic compound, said basic compound present in an amount of 0.01 to 50 mol of basic compound per mole of the total of the metal elements used in the supporting stage.

29. The fixed catalyst according to claim 28, wherein said basic compound is ammonia, a straight-chain alkylamine or an alicyclic alkylamine.

30. The fixed catalyst according to claim 19 wherein said composite of said fixed catalyst is heat treated at a temperature of from 200 to 1100° C.

31. The fixed catalyst according to claim 30, wherein said composite is prepared by supporting at least one metal element belonging to Groups 4 to 11 of the Periodic Table on said carrier and subsequently heat treating the composite at a temperature of from 200 to 1100° C.

* * * * *